United States Patent
Rogers

(10) Patent No.: US 10,508,254 B2
(45) Date of Patent: Dec. 17, 2019

(54) PERMEABILITY AND TRANSFORMATION OF CELLS

(71) Applicant: ARCIS BIOTECHNOLOGY HOLDINGS LIMITED, Daresbury, Warrington Cheshire (GB)

(72) Inventor: Jan Rogers, Chester Cheshire (GB)

(73) Assignee: ARCIS BIOTECHNOLOGY HOLDINGS LIMITED, Daresbury Warrington, Cheshire (GB)

( * ) Notice: Subject to any disclaimer, the term of this patent is extended or adjusted under 35 U.S.C. 154(b) by 465 days.

(21) Appl. No.: 15/120,582

(22) PCT Filed: Feb. 20, 2015

(86) PCT No.: PCT/GB2015/040500
§ 371 (c)(1),
(2) Date: Aug. 22, 2016

(87) PCT Pub. No.: WO2015/124945
PCT Pub. Date: Aug. 27, 2015

(65) Prior Publication Data
US 2018/0305641 A1    Oct. 25, 2018

(30) Foreign Application Priority Data

Feb. 21, 2014    (GB) .................................. 1403107.4

(51) Int. Cl.
| | | |
|---|---|---|
| *C12Q 1/68* | (2018.01) | |
| *C11D 7/50* | (2006.01) | |
| *C07F 7/08* | (2006.01) | |
| *C12N 15/64* | (2006.01) | |
| *C12N 15/79* | (2006.01) | |
| *C12N 15/87* | (2006.01) | |
| *C12N 15/74* | (2006.01) | |

(52) U.S. Cl.
CPC .............. *C11D 7/5009* (2013.01); *C07F 7/08* (2013.01); *C12N 15/64* (2013.01); *C12N 15/74* (2013.01); *C12N 15/79* (2013.01); *C12N 15/87* (2013.01); *C12Q 2527/101* (2013.01); *C12Q 2527/125* (2013.01)

(58) Field of Classification Search
None
See application file for complete search history.

(56) References Cited

U.S. PATENT DOCUMENTS 4,935,342 A * 6/1990 Seligson .................. C07H 1/08
435/270

OTHER PUBLICATIONS

Reddi et al. (PNAS, 1974, 71(5):1648-1652) (Year: 1974).*
Tomasz et al. (PNAS, 1968, 59(1):86-93) (Year: 1968).*
PCT/GB2015/050500 International Search Report and Written Opinion dated Jul. 17, 2017.
Maconi, et al "Niosomes as carriers for tretinoin" Internation Journal of Pharmaceutics, BV, NL, vol. 311, No. 1-2 Mar. 27, 2006, pp. 11-19.
Rajagopal, et al "CTAB-mediated, single-step preparation of competent *Escherichia coli, Bifidobacterium* sp: And Kluyveromyces lactis cells" Meta Gene Dec. 1, 2014, Elsevier NLD, vol. 2, Dec. 1, 2014, pp. 807-818.
Sarkar Suchitra, et al. "Mechanism of artificial transformation of *E. coli* with plasmid DNA: Clues from the influence of ethanol." Current Science (Bangalore), vol. 83, No. 11 Dec. 10, 2002, pp. 1376-1380.
Serafini Fausta et al "An efficient and reproducible method for transformation of genetically recalcitrant bifidobacteria." FEMS Microbiology Letters, vol. 333, No. 2. Aug. 2012, pp. 146-152.
Tu, et al "An improved system for competent cell preparation and high efficiencyplasmid transformation using different *Escherichia coli* strains." Electronic Journal of Biotechnology, vol. 8 No. 1, Apr. 15, 2005, pp. 114-120.

* cited by examiner

*Primary Examiner* — Stephanie K Mummert
(74) *Attorney, Agent, or Firm* — Hoffman Warnick LLC

(57) ABSTRACT

A method of inducing competence in cells, the method comprising contacting the cell with a composition comprising a quaternary ammonium compound including a silicon-containing functional group and a hydrocarbyl-saccharide compound.

11 Claims, No Drawings

PERMEABILITY AND TRANSFORMATION OF CELLS

The present invention relates to methods and compositions for use in the transformation of cells.

The process of DNA uptake by a cell is known as transformation. Transformation results in the genetic alteration of cells by the uptake, incorporation and subsequent translation of exogenous DNA. Methods of transformation are well known in the art and have several applications across medicine, including gene therapy, vaccination and pharmaceuticals, agriculture and research. For example, such methods are used in the genetic engineering of bacteria, yeast, plants and animals.

In the transformation process it is first necessary to isolate the genetic material that is to be taken up by the cell. Methods of isolating the genetic material will be known to the person skilled in the art. These include, amplification of the gene by polymerase chain reaction (PCR), isolation using restriction enzymes and artificial synthesis. The isolated genetic material is then typically combined into a vector, which contains other genetic elements necessary for successful incorporation and/or translation, using recombinant DNA techniques. Such techniques will be well known to the person skilled in the art. Vectors include, for example, plasmids, viral vectors, cosmids, phages and artificial chromosomes.

The DNA is then contacted with the cells. However, in order to take up the DNA from the surroundings, the cells must be in a state of competence. Competent cells are in a special physiological state which enables them to take up exogenous DNA. Competence can be natural, for example about 1% of bacterial cells are naturally competent, or artificially induced.

There are a number of existing methods of artificially inducing competence in cells and these will be known to the person skilled in the art. Procedures for artificially inducing competence involve making the cell passively permeable to DNA by using conditions that do not normally occur in nature.

Some existing methods of transforming cells involved artificially inducing competence and then provided a thermal shock. Other methods of introducing exogenous DNA into cells are also known.

Processes known in the art for achieving transformation include chemical methods, enzymatic treatment, mechanical agitation, electroporation, viral transduction, particle bombardment and transfection.

However drawbacks exist with these methods. Electroporation is one common method but can only be used with short strands of DNA and requires a high degree of purity and repeated washing pre-treatment steps. Particle bombardment can only be used in particular circumstances.

The present invention relates to a new chemical method of inducing competence in cells. Known chemical methods include treatments with calcium or magnesium chloride. However such methods require multiple washing steps and are laborious and time-consuming.

It is an aim of the present invention to provide an alternative method of inducing competence in cells.

According to a first aspect of the present invention there is provided a method of inducing competence in cells, the method comprising contacting the cell with a composition comprising a quaternary ammonium compound including a silicon-containing functional group and a hydrocarbyl-saccharide compound.

The cells may be any suitable cells. The cells may be selected from prokaryotic, eukaryotic or archaeal cells. The cells may be obtained from Gram-positive or Gram-negative bacteria, mycobacteria, *mycoplasma*, fungi, or parasitic organisms; or from animals or plants. The cells may be animal cells, for example cells derived from humans, mammals or other animals. The cells may be plant cells. The cells may be a human or animal tissue cell. The cells may be selected from any region potentially interesting for genetic modification or therapy. For example the cells may be selected from connective, muscle, nervous or epithelial tissue cells. The cells may be obtained from a bodily fluid of a human or animal whose cell content may need to be genetically modified or could act as a vector for cell therapy. For example the cells may be obtained from blood, mucus, sputum, urine, vomit or other excrement.

Exemplary Gram-negative bacteria include, but are not limited to, bacteria of the genera *Bacteroides, Bartonella, Bordetella, Borrelia, Brucella, Campylobacter, Chlamydia, Escherichia, Francisella, Haemophilus, Helicobacter, Klebsiella, Legionella, Leptospira, Moraxella, Neisseria, Pasteurella, Proteus, Pseudomonas, Salmonella, Shigella, Spirillum, Streptobacillus, Treponema, Vibro*, and *Yersinia*. Exemplary Gram-positive bacteria include, but are not limited to, bacteria of the genera *Actinomyces, Bacillus, Clostridium, Corynebacterium, Listeria, Nocardia, Peptostreptococcus, Propionibacterium, Staphylococcus, Streptococcus*, and *Streptomyces*.

Exemplary fungal cells include any species of *Aspergillus* Exemplary yeast cells include, but are not limited to, any species of *Pichia, Saccharomyces, Schizosaccharomyces*, or *Schwanniomyces*

Parasitic cells include, but are not limited to, those belonging to the genera *Acanthamoeba, Ancylostoma, Ascaradia, Babesia, Balamuthia, Balantidium, Brugia, Clonorchis, Cryptosporidium, Dicrocoelium, Dicyotocaulus, Dientamoeba, Diphylobothrium, Dirofilaria, Echinococcus, Echinostoma, Entamoeba, Enterobius, Fasciola, Fascioloides, Giardia, Hymenolepsis, Isospora, Leishmania, Mesocestoides, Moniezia, Necator, Naegleria, Onchocerca, Opisthorchis, Paragonimus, Plasmodium, Rhabditida, Schistosoma, Spirurida, Strongyloides, Taenia, Trichomonas, Trichuris, Toxocara, Trypanosoma, Uncinaria* and *Wuchereria*.

The cells may be connective tissue cells. Connective tissue cells include storage cells such as brown or white adipose cells and liver lipocytes, extracellular matrix (ECM)-secreting cells such as fibroblasts, chondrocytes, and osteoblasts, and blood/immune system cells such as lymphocytes (T lymphocytes, B lymphocytes, or plasma cells), granulocytes such as basophils, eosinophils, and neutrophils, and monocytes. The cells may be an epithelial cell. Epithelial cell types include gland cells specialized for secretion such as exocrine and endocrine glandular epithelial, and surface epithelial cells such as keratinizing and non-keratinizing surface epithelial cells. The cells may be a nervous tissue cell. Nervous tissue cells include glia cells and neurons of the central or peripheral nervous system. The cells may be muscle cells. Muscle tissue cells include skeletal, cardiac, and smooth muscle cells. Many of these cell types can be further divided. The cells may be of endodermal, mesodermal, or ectodermal origin. The cells may be stem cells or mature, differentiated cells. Exemplary stem cells include hematopoietic stem cells, neural stem cells, and mesenchymal stem cells. Exemplary mature, differentiated cell types include adipocytes such as white fat cells or brown fat cells, cardiac myocytes, chondrocytes, endothelial cells, exocrine gland cells, fibroblasts, hepatocytes, keratinocytes, macrophages, monocytes, melanocytes, neurons, neutrophils, osteoblasts, osteoclasts, pancreatic islet cells such as beta cells, skeletal myocytes, smooth muscle cells, B cells, plasma cells, T lymphocytes such as regulatory, cytotoxic, and helper, and dendritic cells.

In some embodiments the cells may be yeast cells.

In preferred embodiments the cells are bacteria cells. Preferably the cells are gram negative bacteria cells. Suitably the cells are gammoproteobacteria cells.

In some preferred embodiments the cells are *Escherichia* cells. Suitably they are *Escherichia Coli* (*E. Coli*) cells.

The method of the present invention preferably involves contacting the composition with cells that are in a phase of pure exponential growth. Techniques for obtaining cells in this stage of growth are known to the person skilled in the art.

The growth of cells, for example bacteria cells can be measured by optical density. Typically the cells used in the method of the present invention have an $OD_{330}$ of from 0.1 to 1.

In the method of the present invention the cells are contacted with a composition comprising a quaternary ammonium compound including a silicon-containing functional group, and a hydrocarbyl-saccharide compound.

Preferably the quaternary ammonium compound including a silicon-containing functional group is a compound of general formula (I):

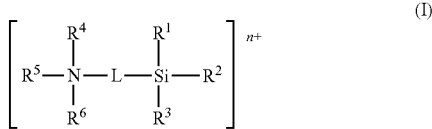

or a derivative salt thereof wherein L is a linking group; each of $R^1$, $R^2$, $R^3$, $R^4$, $R^5$ and $R^6$ is independently selected from H or an optionally substituted alkyl, alkenyl, aryl or alkoxy group; and n is 0 or 1.

It will be appreciated that in embodiments in which n is 1, the species shown in formula (I) is a cationic species.

In such embodiments the species of formula (I) will be present as an adduct or salt including a suitable counterion. However for ease of reference, in this document we may make general reference to compounds of formula (I) and any such reference includes where appropriate any counterion which must be present.

Any suitable counterion may be used. Monovalent counterions are preferred. Suitable counterions include halides and oxyhalo ions for example chloride, bromide, bromite, chlorite, hypochlorite, chlorate, bromate and iodate. In a most preferred embodiment the counterion is a chloride ion.

In this specification any optionally substituted alkyl, alkenyl, aryl or alkoxy group may be optionally substituted with one or more substituents selected from halo, hydroxy, nitro, mercapto, amino, alkyl, alkoxy, aryl, sulfo and sulfoxy.

Preferred substituents which may be present in the alkyl, alkenyl, aryl or alkoxy groups defined herein are halogens, in particular fluorine. In particular each of $R^1$, $R^2$, $R^3$, $R^4$, $R^5$ or $R^6$ may comprise fluoroalkyl or fluoroalkoxy groups which may comprise one or more fluorine atoms.

Each of $R^1$, $R^2$ and $R^3$ is independently selected from an optionally substituted alkyl, alkenyl, aryl or alkoxy group. Preferably at least one of $R^1$, $R^2$ and $R^3$ is an optionally substituted alkoxy group. More preferably each of $R^1$, $R^2$ and $R^3$ is an optionally substituted alkoxy group, most preferably each is an unsubstituted alkoxy group. The alkyl group of the alkoxy group may be straight chained or branched. Preferably each of $R^1$, $R^2$ and $R^3$ is an alkoxy group having from 1 to 20 carbon atoms, preferably from 1 to 16 carbon atoms, more preferably from 1 to 12 carbon atoms, preferably from 1 to 8 carbon atoms, suitably from 1 to 6 carbon atoms, more preferably from 1 to 4 carbon atoms.

In preferred embodiments each of $R^1$, $R^2$ and $R^3$ is independently selected from methoxy, ethoxy, propoxy, butoxy and isomers thereof. Most preferably each of $R^1$, $R^2$ and $R^3$ is selected from methoxy, ethoxy and isopropoxy. Preferably each of $R^1$, $R^2$ and $R^3$ is selected from methoxy and ethoxy. Most preferably each of $R^1$, $R^2$ and $R^3$ is methoxy. Preferably each of $R^1$, $R^2$ and $R^3$ is the same.

$R^4$ and $R^6$ is preferably an alkyl group having from 1 to 8 carbon atoms, most preferably 1 to 6 carbon atoms, more preferably 1 to 4 carbon atoms. $R^4$ and $R^6$ may suitably be selected from methyl, ethyl, propyl, butyl and isomers thereof. Preferably $R^4$ and $R^6$ is methyl or ethyl. Most preferably $R^4$ and $R^6$ is methyl.

Preferably $R^5$ is an alkyl group having from 8 to 30 carbon atoms, for example from 10 to 26 carbon atoms, suitably from 12 to 24 carbon atoms, preferably from 14 to 22 carbon atoms, suitably from 16 to 20 carbon atoms, for example 17 to 19 carbon atoms, suitably 18 carbon atoms.

L is a linking group. It may suitably be a bond or an optionally substituted alkylene, alkenylene or arylene group. Preferably L is an optionally substituted alkenylene group. It may be substituted along the chain or within the chain. For example L may be an ether linking moiety, i.e. a group of formula $O(CH_2)_n$ in which n is 1 to 12, preferably 1 to 6.

Preferably L is an unsubstituted alkylene group, more preferably an alkylene group having 1 to 12 carbon atoms, preferably 1 to 10 carbon atoms, suitably 1 to 8 carbon atoms, for example 2 to 8 carbon atoms, more preferably 2 to 6 carbon atoms, suitably 2 to 5 carbon atoms for example 2 to 4 carbon atoms. In especially preferred embodiments L is a propylene group.

In especially preferred embodiments of the compound of formula (I), $R^1$, $R^2$ and $R^3$ are each $C_1$ to $C_4$ alkoxy, L is a $C_2$ to $C_5$ alkylene group, $R^4$ and $R^6$ are each $C_1$ to $C_4$ alkyl groups and $R^5$ is a $C_{12}$ to $C_{24}$ alkyl group.

Most preferably the compound of formula (I) is the compound shown in formula (II). This compound is commercially available as a solution in methanol.

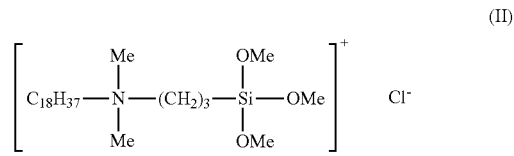

The composition contacted with the cells in the method of the present invention preferably comprises at least 0.001 wt % of a quaternary ammonium compound including a silicon-containing functional group, preferably at least 0.005 wt %, more preferably at least 0.01 wt %, and more preferably at least 0.05 wt %.

The quaternary ammonium compound including a silicon-containing functional group preferably comprises up to 10 wt % of the composition contacted with the cells, suitably up to 5 wt %, preferably up to 2.5 wt %, preferably up to 1.5 wt %, more preferably up to 1.2 wt %, and more preferably up to 1 wt %, for example up to 0.9 wt %.

The composition contacted with the cells in the method of the present invention also includes a hydrocarbyl-saccharide compound.

By hydrocarbyl-saccharide compound we mean to refer to a compound including a hydrocarbyl group and a saccharide moiety.

The hydrocarbyl group may be bound to the saccharide moiety via a carbon-carbon bond or via a carbon-oxygen bond. Preferably it is bound to the saccharide moiety via a carbon-oxygen bond, for example via an ester linkage or an ether linkage. Most preferably it is bound to the oligosaccharide moiety via an ether linkage. Thus in preferred embodiments the hydrocarbyl-saccharide compound is a hydrocarbyl ether of a saccharide moiety.

The hydrocarbyl-saccharide compound may include one or more hydrocarbyl groups. Preferably it comprises one hydrocarbyl group. The hydrocarbyl group may be an optionally substituted alkyl, alkenyl or alkynylene group. Most preferably it is an optionally substituted alkyl group. Suitable substituents include halo, hydroxy, nitro, mercapto, amino, alkyl, alkoxy, aryl, sulfo and sulfoxy. Any substitution may be within the chain or along it, for example the chain may include an ether linkage.

Preferably the hydrocarbyl group is an unsubstituted alkyl group. It may be straight chained or may be branched. Most preferably it is straight chained. Especially preferred hydrocarbyl groups are alkyl groups having from 1 to 30 carbon atoms, preferably 2 to 24 carbon atoms, more preferably from 4 to 20 carbon atoms, suitably from 4 to 16 carbon atoms, preferably from 6 to 14 carbon atoms, for example from 6 to 12 carbon atoms and most preferably from 8 to 10 carbon atoms. Preferred are straight chained alkyl groups having from 6 to 12 carbon atoms.

The saccharide moiety of the hydrocarbyl oligosaccharide species may include from 1 to 10 monosaccharide species. Thus it may be a monosaccharide unit, a disaccharide unit or an oligosaccharide unit. Preferably the saccharide moiety comprises from 2 to 8, suitably from 2 to 6, preferably from 2 to 5, for example 3 or 4 monosaccharide units. Any suitable monosaccharide unit may be included. Preferred saccharides include allose, altrose, glucose, mannose, gulose, idose, galactose and talose.

Mixtures of two or more monosaccharides may be present in the saccharide moiety. Preferably the saccharide moiety comprises glucose. More preferably all of the monosaccharide units present in the saccharide moiety are glucose.

In a preferred embodiment the hydrocarbyl-saccharide compound is an alkyl polyglucoside (APG), preferably a monoalkyl-polyglucoside. Suitably the hydrocarbyl-saccharide compound is a compound of general formula (III):

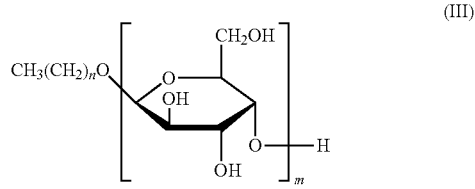

(III)

wherein n is from 5 to 12, preferably from 6 to 10, more preferably from 7 to 9 and m is from 1 to 6, preferably from 2 to 5, more preferably 3 or 4.

The hydrocarbyl saccharide compound is suitably present in the composition contacted with the cell or capsid in an amount of at least 0.001 wt %, preferably at least 0.005 wt %, more preferably at least 0.01 wt %, and more preferably at least 0.02 wt %, for example at least 0.03 wt %.

The hydrocarbyl saccharide compound may be present in the composition contacted with the cell or capsid in an amount of up to 10 wt % of the composition, suitably up to 5 wt %, preferably up to 2.5 wt %, preferably up to 1.5 wt %, more preferably up to 1.2 wt %, and more preferably up to 1 wt %, for example up to 0.9 wt %.

The weight ratio of the quaternary ammonium compound including a silicon-containing functional component to the hydrocarbyl saccharide compound is preferably from 1:10 to 10:1, preferably from 1:5 to 5:1, preferably from 1:3 to 3:1, and more preferably from 1:2.5 to 2.5:1. In some embodiments the weight ratio of the quaternary ammonium compound including a silicon-containing functional component to the hydrocarbyl saccharide compound is from 1:0.8 to 2.5:1.

Preferably the composition is contacted with the cells is aqueous. In especially preferred embodiments water comprises at least 90 wt %, more preferably at least 95 wt % or at least 99 wt % of all solvents present in the compositions.

The composition may comprise a buffer. Any suitable buffer can be used. Preferred buffers are biologically acceptable buffers. Examples of suitable buffers include but are not limited to N-(2-acetamido)-aminoethanesulfonic acid, acetate, N-(2-acetamido)-iminodiacetic acid, 2-aminoethanesulfonic acid, ammonia, 2-amino-2-methyl-1-propanol, 2-amino-2-methyl-1,3-propanediol, N-(1,1-dimethyl-2-hydroxyethyl)-3-amino-2-hydroxypropanesulfonic acid, N,N-bis-(2-hydroxyethyl)-2-aminoethanesulfonic acid, sodium hydrogen carbonate, N,N'-bis(2-hydroxyethyl)-glycine, [bis-(2-hydroxyethyl)-imino]-tris-(hydroxymethylmethane), 1,3-bis[tris(hydroxymethyl)-methylamino]propane, boric acid, dimethylarsinic acid, 3-(cyclohexylamino)-propanesulfonic acid, 3-(cyclohexylamino)-2-hydroxyl-1-propanesulfonic acid, sodium carbonate, cyclohexylaminoethanesulfonic acid, citrate, 3-[N-bis(hydroxylethyl)amino]-2-hydroxypropanesulfonic acid, formate, glycine, glycylglycine, N-(2-hydroxyethyl)-piperazine-N'-ethanesulfonic acid, N-(2-hydroxyethyl)-piperazine-N'-3-propanesulfonic acid, N-(2-hydroxyethyl)-piperazine-N'-2-hydroxypropanesulfonic acid, imidazole, malate, maleate, 2-(N-morpholino)-ethanesulfonic acid, 3-(N-morpholino)-propanesulfonic acid, 3-(N-morpholino)-2-hydroxypropanesulfonic acid, phosphate, piperazine-N,N'-bis(2-ethanesulfonic acid), piperazine-N,N'-bis(2-hydroxypropanesulfonic acid), pyridine, succinate, 3-{[tris(hydroxymethyl)-methyl]amino}-propanesulfonic acid, 3-[N-tris(hydroxymethyl)-methylamino]-2-hydroxypropanesulfonic acid, 2-aminoethanesulfonic acid, triethanolamine, 2-[tris(hydroxymethyl)-methylamino]-ethanesulfonic acid and, N-[tris(hydroxymethyl)-methyl]-glycine, tris(hydroxymethyl)-aminomethane, One especially preferred buffer is tris(hydroxymethyl)-aminomethane (TRIS). A TRIS buffer may be included as the hydrochloride salt or the ammonium salt.

The composition contacted with the cells preferably has a pH of from 5 to 8, more preferably from 6 to 7.5.

In the method of the first aspect of the present invention the cells are suitably provided as an aqueous suspension undergoing exponential growth. This suspension is suitably contacted with the composition comprising a quaternary ammonium compound including a silicon-containing functional group and a hydrocarbyl saccharide compound in a volume ratio of from 10000:1 to 1:10, preferably from 1000:1 to 1:1, suitably from 100:1 to 5:1.

In the method of the first aspect of the present invention the composition is preferably contacted with the cells for a period of at least 10 seconds, suitably at least 30 seconds, preferably at least one minute, more preferably at least two minutes, suitably at least five minutes, for example at least ten minutes. In the method of the present invention the composition may be contacted with the cells for a period of up to twelve hours, suitably up to six hours, preferably up to three hours, more preferably up to 1 hour, for example up to thirty minutes or up to twenty minutes.

In the method of the present invention the composition is preferably contacted with the cells at ambient temperature.

According to a second aspect of the present invention there is provided a method of transformation of cells, the method comprising the steps of:
(i) contacting the cells with a composition comprising a quaternary ammonium compound including a silicon-containing functional group and a hydrocarbyl saccharide compound;
(ii) adding a source of exogenous DNA to the cells; and
(iii) thermally shocking the cells.

In some embodiments step (ii) may be carried out before step (i) and step (i) may involve contacting the composition with a mixture of cells and a source of exogenous DNA.

In preferred embodiments step (ii) is carried out after step (i).

Step (iii) is suitably carried out after steps (i) and (ii).

Preferred features of step (i) of the method of the second aspect of the invention are as defined in relation to the first aspect.

Suitably in step (ii) of the method of the present invention the source of exogenous DNA is added directly to the composition obtained in step (i). Thus in preferred embodiments no purification steps are carried out following step (i).

The exogenous DNA referred to in step (ii) is exogenous to the cells used in step (i).

Any suitable source of exogenous DNA may be used. These will be known to the person skilled in the art. The exogenous DNA may be obtained from plants or animals. It may be synthetic DNA or copied DNA or it may be natural or isolated DNA.

Suitably the source of exogenous DNA may be recombinant DNA and precloned DNA.

In preferred embodiments the exogenous DNA is combined into a vector. Suitable vectors will be known to the person skilled in the art. Suitable vectors include plasmids, viral vectors, cosmids and artificial chromosomes.

Preferably the vector is a plasmid. Thus in preferred embodiments step (ii) comprises contacting the composition obtained in step (i) with a plasmid carrying exogenous DNA.

Step (iii) involves thermally shocking the cells. This is a standard technique which will be known to the person skilled in the art. A suitable thermal shock treatment method is described by Maniartis et al in current protocols in Molecular Biology.

Typically a thermal shock process involves keeping cells at about 45° C. for 5 to 40, for example about 15 minutes, then heating to about 42° C. for a period of 1 to 15, for example about 4 minutes; and then cooling to about 4° C. again for a period of 1 to 20, for example 5 minutes.

According to a third aspect of the present invention there is provided a kit for transformation of cells, the kit comprising a composition comprising a quaternary ammonium compound including a silicon-containing functional group and a hydrocarbyl-saccharide compound; and a source of exogenous DNA.

Preferred features of the kit of the third aspect of the present invention are as defined in relation to the first and second aspects.

The method of the present invention may be used in a wide variety of applications. For example it may be used for the cloning of recombinant DNA, in site-directed mutagenesis, to test in vitro systems for interference RNA, as a potential; drug delivery system, in gene therapy, in gene engineering or in vaccine production.

The invention will now be further defined with reference to the following non-limiting examples.

EXAMPLE 1

An *E. coli* propriety strain was treated with an aqueous test composition comprising 0.08 wt % of the quaternary ammonium compound of formula (II) described in the specification and 0.08 wt % of the monoalkyl polyglucoside compound of formula (III) described in the specification.

Commercially available InvitroGen competent cells were tested as a comparative composition.

Treatment was performed over an ON culture diluted to an $OD_{330}$ of 0.01 and grown again to an $OD_{330}$ of 0.11

The resulting exponentially growing cells were thoroughly mixed with the test compositions and the control composition and kept on ice for 15 minutes, before performing the thermal shock as described by Maniatis et al. in *Current Protocols in Molecular Biology*. An analogous procedure was carried out using the control samples.

A commercially available vector, pVC19 was used and a sample of cloned DNA. These were added to the cooled composition prior to the thermal shock. In each case the DNA sample was added 5 minutes after the cells were put on ice, allowing the DNA to interact with the cells for 10 minutes prior to the thermal shock.

pUC19 with no cloned insert is used as a positive control. The clean plasmid with no cloned DNA is the default choice for its reduced toxicity and impairment in terms of cell metabolism and recombination machinery.

In treatment A, 480 μL of cells were mixed with 20 μL test composition.

In treatment B, 470 μL of cells were mixed with 30 μL of test composition.

| Treatment | Number of transformants |
| --- | --- |
| InvitroGen competent cells/pUC19 control | 78 |
| InvitroGen competent cells/no DNA (−ve control) | 0 |
| Treatment A | 3 |
| Treatment B | 16 |

EXAMPLE 2

A further *E. coli* strain (DH5α F') was treated using the same test composition and procedure as example 1 and compared with commercially available InvitroGen competent cells.

Again, the treatment was performed over an ON culture diluted to an $OD_{330}$ of 0.01 and grown again to an $OD_{330}$ of 0.11

The resulting exponentially growing cells were thoroughly mixed with the composition and kept on ice for 15 minutes, before adding the cloned DNA and performing the thermal shock as described by Maniatis et al. in *Current Protocols in Molecular Biology*. The cloned DNA was added 5 minutes after the cells were put on ice, allowing the DNA to interact with the cells for 10 minutes prior to the thermal shock.

| Treatment | Number of transformants |
|---|---|
| InvitroGen competent cells/pUC18 control | 80 |
| InvitroGen competent cells/no DNA (−ve control) | 0 |
| Treatment A | 9 |
| Treatment B | 29 |

EXAMPLE 3

A proprietary *E. coli* strain was treated with the same test composition as example 1 and compared with commercially available InvitroGen competent cells.

Treatment was performed over an ON culture diluted to an $OD_{330}$ of 0.01 and grown again to an $OD_{330}$ of 0.11

The resulting exponentially growing cells were thoroughly mixed with the test composition and kept on ice for 15 minutes, before adding the cloned DNA and performing the thermal shock as described by Maniatis et al. in *Current Protocols in Molecular Biology*. The cloned DNA was added 5 minutes after the cells were put on ice, allowing the DNA to interact with the cells for 10 minutes prior to the thermal shock.

| Treatment | Number of transformants |
|---|---|
| InvitroGen competent cells/+pUC19 control | >50 |
| InvitroGen competent cells/no DNA (−ve control) | 0 |
| Treatment B | 7 |

EXAMPLE 4

*E. coli* standard strain DH5α F' was treated with the same composition test and procedure as example 1 and compared with commercially available InvitroGen competent cells.

Treatment was performed over an ON culture diluted to an $OD_{330}$ of 0.01 and grown again to an $OD_{330}$ of 0.11.

The resulting exponentially growing cells were thoroughly mixed with the ARCIS sample(s) and kept on ice for 15 minutes, before adding the cloned DNA and performing the thermal shock as described by Maniatis et al. in *Current Protocols in Molecular Biology*. The cloned DNA was added 5 minutes after the cells were put on ice, allowing the DNA to interact with the cells for 10 minutes prior to the thermal shock.

| Treatment | Number of transformants |
|---|---|
| InvitroGen competent cells + pUC18 control | 70 |
| InvitroGen competent cells no DNA (−ve control) | 0 |
| Treatment A | 2 |
| Treatment B | 12 |

The invention claimed is:

1. A method of inducing competence in cells, the method comprising contacting the cell with a composition comprising a quaternary ammonium compound including a silicon-containing functional group and a hydrocarbyl-saccharide compound of general formula (III):

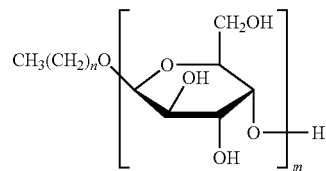

(III)

wherein n is from 5 to 12, preferably from 6 to 10, more preferably from 7 to 9 and m is from 1 to 6, preferably from 2 to 5, more preferably 3 or 4.

2. A method according to claim 1 wherein the cells are bacteria cells.

3. A method according to claim 2 wherein the cells are gram negative bacteria cells.

4. A method according to claim 1 wherein the cells are yeast cells.

5. A method according to claim 1 wherein the cells are prokaryotic cells.

6. A method according to claim 1 wherein the cells are eukaryotic cells.

7. A method according to claim 1 wherein the quaternary ammonium compound including a silicon-containing functional group is a compound of general formula (I):

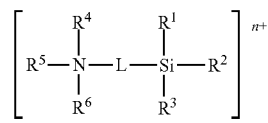

(I)

or a derivative salt thereof wherein L is a linking group; each of $R^1$, $R^2$, $R^3$, $R^4$, $R^5$ and $R^6$ is independently selected from H or an optionally substituted alkyl, alkenyl, aryl or alkoxy group; and n is 0 or 1.

8. A method according to claim 7 wherein the quaternary ammonium compound including silcon-containing functional group is a compound of formula II:

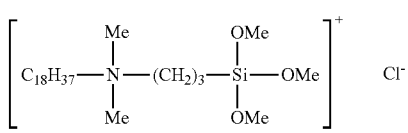

(II)

9. A method of transformation of cells, the method comprising the steps of:
   (i) contacting the cells with a composition comprising a quaternary ammonium compound including a silicon-containing functional group and a hydrocarbyl-saccharide compound of general formula (III):

(III)

wherein n is from 5 to 12, preferably from 6 to 10, more preferably from 7 to 9 and m is from 1 to 6, preferably from 2 to 5, more preferably 3 or 4;

(ii) adding a source of exogenous DNA to the cells; and
(iii) thermally shocking the cells.

10. A method according to claim 9 wherein the source of exogenous DNA is a plasmid carrying exogenous DNA.

11. A kit for transformation of cells, the kit comprising:
a composition comprising a quaternary ammonium compound including a silicon-containing functional group and a hydrocarbyl-saccharide compound of general formula (III):

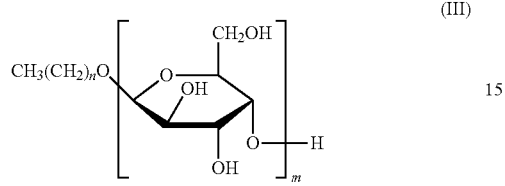

wherein n is from 5 to 12, preferably from 6 to 10, more preferably from 7 to 9 and m is from 1 to 6, preferably from 2 to 5, more preferably 3 or 4; and
a source of exogenous DNA.

* * * * *